United States Patent
Matoba

(10) Patent No.: US 7,289,598 B2
(45) Date of Patent: Oct. 30, 2007

(54) X-RAY FLUORESCENT ANALYSIS APPARATUS

(75) Inventor: Yoshiki Matoba, Chiba (JP)

(73) Assignee: SII Nano Technology Inc., Chiba (JP)

( * ) Notice: Subject to any disclaimer, the term of this patent is extended or adjusted under 35 U.S.C. 154(b) by 0 days.

(21) Appl. No.: 11/264,403

(22) Filed: Nov. 1, 2005

(65) Prior Publication Data

US 2006/0093085 A1 May 4, 2006

(30) Foreign Application Priority Data

Nov. 2, 2004 (JP) .............................. 2004-318763

(51) Int. Cl.
*G01N 23/223* (2006.01)
*H05G 1/38* (2006.01)

(52) U.S. Cl. ............................ 378/46; 378/42; 378/48; 378/96

(58) Field of Classification Search ............ 378/44–48, 378/96, 97, 207, 42, 119, 121, 137, 138, 141, 378/142, 144, 210; 250/458.1, 459.1
See application file for complete search history.

(56) References Cited

U.S. PATENT DOCUMENTS

| | | | | |
|---|---|---|---|---|
| 6,005,915 A | * | 12/1999 | Hossain et al. ................. | 378/86 |
| 6,115,450 A | * | 9/2000 | Hasegawa ..................... | 378/50 |
| 6,173,037 B1 | * | 1/2001 | Brouwer ...................... | 378/45 |
| 6,370,220 B1 | * | 4/2002 | Stoop .......................... | 378/45 |
| 6,765,205 B2 | * | 7/2004 | Ochiai et al. ................ | 250/310 |
| 7,016,462 B1 | * | 3/2006 | Keville et al. ................ | 378/47 |
| 2002/0154732 A1 | * | 10/2002 | Grodzins et al. ............. | 378/46 |
| 2005/0053193 A1 | * | 3/2005 | Hasegawa ..................... | 378/46 |
| 2005/0087699 A1 | * | 4/2005 | Miyake ..................... | 250/492.1 |
| 2006/0029182 A1 | * | 2/2006 | Tani et al. ..................... | 378/45 |

FOREIGN PATENT DOCUMENTS

| | | |
|---|---|---|
| JP | H03-221852 | 9/1991 |
| JP | 2001-133419 | 5/2001 |
| JP | 2004-150990 | 5/2004 |
| WO | WO 03/043497 A1 * | 5/2003 |

OTHER PUBLICATIONS

"Handbook for X-ray Fluorescent Analysis," 4th edition, Regaku Corporation, Jul. 1993, pp. 63-65.
Yoichi Gohshi "Lower Limit of Quantification with X-ray Fluorescence Analysis" Mar. 10, 1994.
Japanese Office Action dated Jun. 12, 2007.

* cited by examiner

*Primary Examiner*—Edward J. Glick
*Assistant Examiner*—Anastasia S. Midkiff
(74) *Attorney, Agent, or Firm*—Brinks Hofer Gilson & Lione

(57) ABSTRACT

The change in the sample size and a change in background intensity due to the coexisting element are measured in real time to thereby automatically change a measurement time, the detection lower limit is kept constant, so that a fluorescent X-ray apparatus is provided that is capable of measuring every time in the same detection lower limit even in a case where there have existed a change in size of a sample, a change in sensitivity due to a difference in main ingredient, and a change of a magnitude in background due to an influence of a coexisting element.

8 Claims, 2 Drawing Sheets

Detection lower limit $= 3 * (\text{BG Intensity}/\text{Measurement time})^{1/2} /\text{Sensitivity}$

X-RAY FLUORESCENT ANALYSIS APPARATUS

This application claims priority under 35 U.S.C. §119 to Japanese Patent Application No. 2004-318763 filed Nov. 2, 2004, the entire content of which is hereby incorporated by reference.

BACKGROUND OF THE INVENTION

The present invention relates to an X-ray fluorescent analysis apparatus in which a sample is irradiated with X-rays, which excites fluorescent X-rays out from the sample, and the energy and intensity of the fluorescent X-rays are then measured to determine the element composition of the sample.

The conventional X-ray fluorescent analysis apparatuses operate for a fixed measurement time when analyzing resins composed of C, O, H and the like to determine the existence and concentration of heavy metals, such as Cd and Pd, contained in the resins by very small amounts in the resins (for example, JP-A-2004-150990).

A X-ray fluorescent analysis apparatus is used to analyze resins composed of C, O, H and the like to determine the existence and the concentration of heavy metals, such as Cd and Pd, contained in the resins by very small amounts. In analyzing such resins, however, the lower limit of detection level of the apparatus changes, depending on the sizes of the samples. The lower detection limit also changes due to changes in the detection sensitivity, which changes depending on the kinds of the main components of the samples, or due to changes in the magnitude of background energy caused by the existence of other elements coexisting in the samples. In order to confirm the existence of very small amounts of metals contained in the samples, it is important to maintain the lower detection limit at a constant level for each analysis.

It is an object of the present invention to solve the above problems and provide a system which maintains the lower detection limit at a constant level for every analysis, irrespective of sample sizes, the kinds of main components of samples which affect the detection sensitivity, or the kinds of coexisting elements which affect the magnitude of the background energy.

SUMMARY OF THE INVENTION

In order to solve the above problem, the X-ray fluorescent analysis apparatus of the present invention stores an equation defining the lower detection limit in its software algorism and, upon detection of a cause to affect the lower detection limit, varies the length of the measurement time to thereby maintain the lower detection limit at a constant level for every analysis.

The above equation concerning the lower detection limit may be exemplarily defined as follows:

The "BG intensity" appearing in the equation means the intensity of background energy measured at the spectral position of a fluorescent X-ray at which a referenced heavy metal expresses its energy. This background intensity changes in its magnitude depending on the kinds of elements coexisting in the sample. For example, in a case where the energy of the referenced heavy metal is expressed at a position spectrally close to the energy of a coexisting element in the detected fluorescent X-ray, the spectral distribution representing the energy of the coexisting element overlaps the spectral distribution of the referenced heavy metal, and thereby the background energy in the fluorescent X-ray at the spectral position of the referenced heavy metal is intensified.

Further, the intensity of background energy also changes as the intensity of the primary X-ray irradiated to the sample to excite the fluorescent X-ray changes. The relationship between the intensity of the primary X-ray and a sensitivity coefficient is linear.

The "sensitivity" appearing in the equation means the relationship between the concentration of the referenced heavy metal and the intensity of the spectral energy of the referenced heavy metal in the fluorescent X-ray. This relationship is affected by the size of the sample. Basically, the sensitivity coefficient becomes large as the sample size becomes large, and the sensitivity coefficient becomes small as the size becomes small.

Further, the sensitivity coefficient also changes as the intensity of the primary X-ray irradiated to the sample to excite the fluorescent X-ray changes. The relationship between the intensity of the primary X-ray and the sensitivity coefficient is linear.

The X-ray fluorescent analysis apparatus of the present invention automatically detects a change of the intensity of background energy and a change of the sensitivity coefficient and automatically adjusts the measurement time period to thereby maintain the lower detection limit at a constant level irrespective of the kinds and/or sizes of samples.

The present invention may further be explained as follows.

The apparatus according to the present invention has a function to automatically detect the intensity of background energy in the fluorescent X-ray at the spectral position of the referenced heavy metal. This function enables the apparatus to detect a change of the intensity of background energy caused by the neighboring spectral energies from coexisting elements, then reflect the change in the equation and adjust the measurement time period to maintain the lower detection limit at a constant level.

Additionally, the apparatus according to the present invention has a function to automatically detect the size of a sample, although approximately. This function enables the apparatus to detect a change of the sensitivity coefficient caused by a change in the size of a sample, then reflect the change in the equation and adjust the measurement time period to maintain the lower detection limit at a constant level.

Further, in the X-ray fluorescent analysis apparatus, its detection system generally has a limitation in the detectable intensity of X-rays. Therefore, in order to achieve an efficient detection, it is necessary to change the intensity of the primary X-ray irradiated onto the sample. However, if the intensity of the primary X-ray changes, so does the sensitivity coefficient. The apparatus according to the present invention can reflect the change of the sensitivity coefficient in the equation and adjust the measurement time period to maintain the lower detection limit at a constant level.

DETAILED DESCRIPTION OF THE PREFERRED EMBODIMENT

Figures 1, 2:
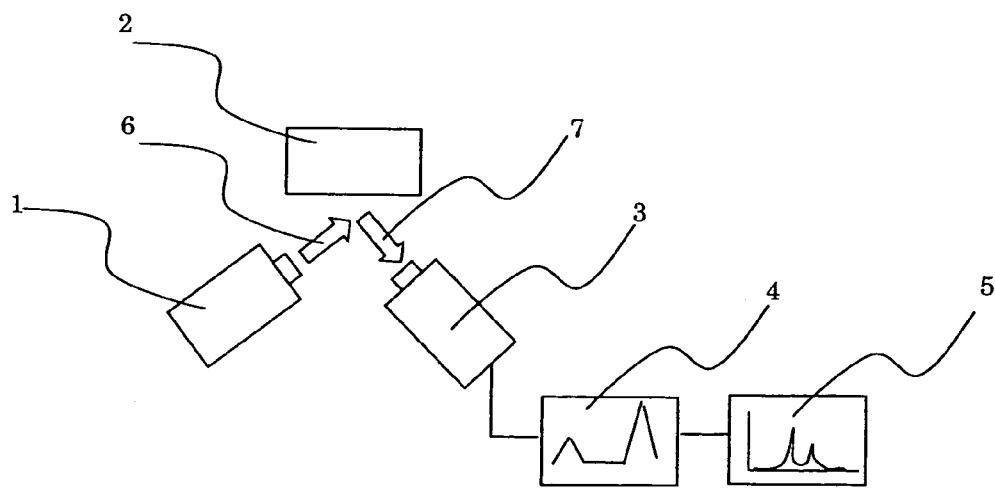
FIG. 1 is a schematic diagram showing the general configuration of an X-ray fluorescent analysis apparatus.
FIG. 2 is an equation for calculating the detection lower limit.

An embodiment of the present invention will be explained with reference to the attached drawings. FIG. 1 is a schematic diagram showing the general configuration of an X-ray fluorescent analysis apparatus. In FIG. 1, a primary X-ray 6 is irradiated onto a sample 2 from an X-ray source 1, which excites a fluorescent X-ray 7 out from the sample 2. The fluorescent X-ray 7 has spectral characteristics attributable to the elements in the sample and enters an X-ray detector 3. The detector 3 converts the X-ray into an electric signal which is processed by a waveform shaping circuit 4 into a signal with peaks whose heights are proportional to the energies, whereby it becomes possible to detect energies of the X-ray and their numbers (intensities). The information regarding the energies and intensities is displayed as a spectrum 5.

FIG. 2 explains the calculation method of the present invention for calculating the lower detection limit. The equation is reproduced below:

$$lowerDetectionLimit = \frac{3 \times \sqrt{\frac{BGIntensity}{MeasurementTime}}}{Sensitivity}$$

The equation of the present invention as shown in FIG. 2 defines the relationship among the lower detection limit, the intensity of background energy, the detection time period and the sensitivity. In other words, according to the equation, the lower detection limit is a function only of the measurement time period, the intensity of background energy and the sensitivity.

Figure 3:
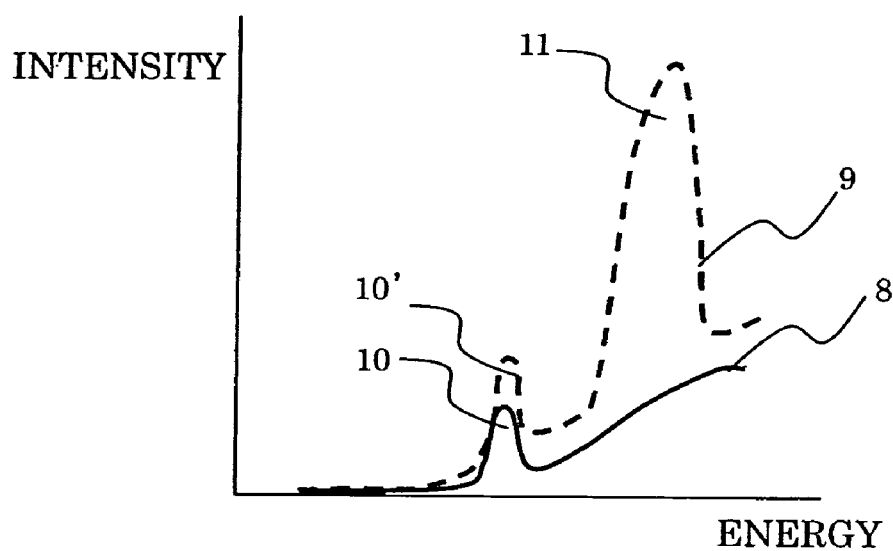
FIG. 3 is a graph showing an exemplary spectrum of the fluorescent X-ray representing Cd and other coexisting elements.

FIG. 3 is an enlarged view showing a part of the spectrum 5 shown in FIG. 1. A solid line 8 represents the spectrum of a sample containing Cd whose concentration is predetermined, and a peak 10 is an energy peak of Cd. The solid line 8 is used as a reference spectrum. First, the intensity of background energy in the Cd spectrum is calculated. Using Equation (1) noted below, the sensitivity is calculated from the background intensity, the gross intensity and the concentration of Cd. The intensity of background energy may be calculated, for instance, by calculating the energy intensities of X-rays detected outside the spectrum distribution including the Cd peak and, from the information showing the intensities detected on both sides of the distribution, forming an equation represented by Y=AX+B. The intensity of background energy is derived by integrating the area. Other methods may be used to calculate the intensity of background energy.

$$Sensitivity = \frac{(GrossIntensity - BackgroundInstensity)}{Concentration} \quad (1)$$

Thus, given a measurement time period, the lower detection limit can be determined, using the equation shown in FIG. 2. In other words, it becomes possible to calculate a measurement time period necessary to achieve the required lower detection limit.

A dotted line 9 in FIG. 3 represents the spectrum of a sample in which a large amount of another element 11, Sb, coexists in the sample. If the concentration of Cd contained in the sample coincides with the concentration of Cd contained in the reference sample, the spectrum pattern exhibited by the sample, excepting the peak caused by the element 11, should match the spectrum pattern exhibited by the reference sample. However, since a large amount of Sb is contained in the sample, the intensity of background energy increases at the spectral position representing the energy of Cd. To rectify this, the intensity of background energy in the spectrum shown by the dotted line 9 at the spectral peak position of Cd is calculated. The calculated background intensity is used in the equation of FIG. 2. The equation borrows the sensitivity from the reference spectrum. The equation thereby yields the necessary measurement time period, given the required lower detection limit.

Figure 4:
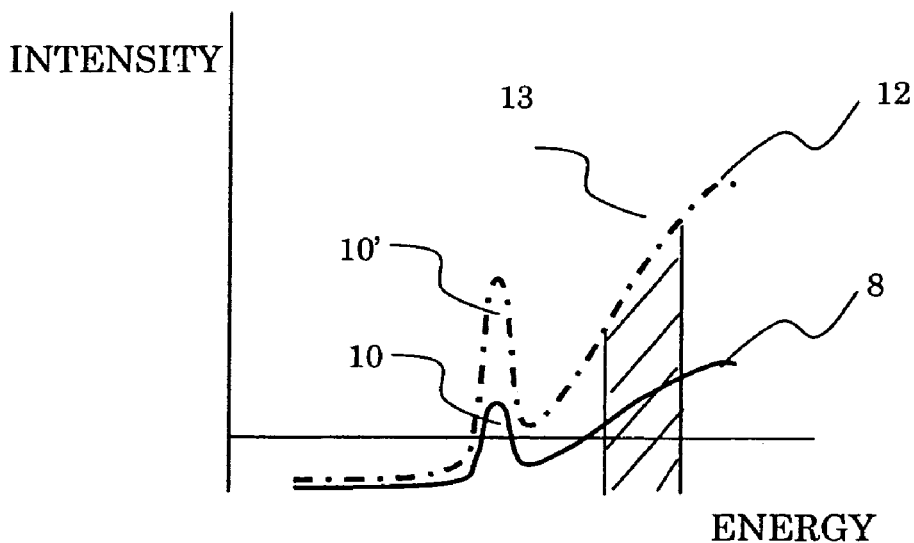
FIG. 4 is a graph showing an exemplary spectrum of the same fluorescent X-ray and another spectrum observed when the size of the sample is changed.

FIG. 4 is an enlarged view from FIG. 1 focusing on the spectrum energies of Cd contained in samples whose sizes are different. The solid line 8 shows the spectrum pattern exhibited by the reference sample in which the concentration of Cd is predetermined. The reference spectrum comprises the spectral peak 10 representing Cd and another portion 13 of the spectrum showing the intensity of scattered X-ray energy. An alternate short and long dash line 12 shows a spectrum pattern of a larger sample which comprises the spectral peak 10' representing Cd and the corresponding portion 13 representing the intensity of scattered X-ray energy. Comparisons to the reference spectrum indicate that the larger the sample size becomes, the more significant the intensity of the fluorescent X-ray at the spectral peak position of Cd becomes. In other words, the sensitivity coefficient becomes large. Further, as the sample size increases, the intensity of the background energy at the spectral position of Cd and the intensity of the scattered X-ray energies at other portions of the spectrum also increase. It is known that given a constant concentration of Cd in the sample, as the sample size changes, so do substantially proportionally the intensity of the fluorescent X-ray at the spectral position of Cd and the intensities of the background energy at the spectral position of Cd and at the other portion 13 of the spectrum. Therefore, the increase rate of the intensity of the scattered X-ray energy at the portion 13 of the spectrum is measured and multiplied to the sensitivity coefficient and the background intensity of the reference spectrum. Using these adjusted sensitivity and the background intensity, it becomes possible to calculate the measurement time period necessary to achieve the required lower detection limit. In other words, even if the sample size changes, it becomes possible to maintain the lower detection lower limit at a constant level by altering the measurement time period. For example, suppose that the intensity of the scattered X-ray energy near the spectral peak of Cd increases by a times. The intensity of background energy increases by a times. So does the sensitivity. If the measurement time period is unchanged, the lower detection limit would change from that of the reference spectrum to $$\frac{1}{\sqrt{\alpha}}.$$

Thus, in order to keep the lower detection limit constant, the detection time period is changed accordingly to Further, the apparatus shown in FIG. 1 according to the present invention can keep the lower detection limit constant, irrespective of not only a change of the sample size, but also a change of the intensity of the primary X-ray 6. The detector used in the X-ray fluorescent analysis apparatus as shown in FIG. 1 is generally limited in detecting a high intensity X-ray within a unit time period. If another element coexists in the sample at a high concentration, a large amount of fluorescent X-ray from the element will enter the detector. To prevent this, it is necessary to lower the output from the X-ray tube 1. Suppose that the output of the X-ray tube changes by $\beta$. Then, the measurement time period will be changed by inverse $\beta$ to maintain the lower detection limit at a constant level.

What is claimed is:

1. A method being implemented in an X-ray fluorescent analysis apparatus for maintaining a lower detection limit at a constant level for respective analyses, comprising:
   determining a reference intensity of background energy and a reference sensitivity by analyzing a reference sample with the X-ray fluorescent analysis apparatus, wherein the reference sample contains at least one reference element at a known concentration;
   initiating an analysis on a sample using the X-ray fluorescent analysis apparatus;
   determining an intensity of background energy and a sensitivity for the analysis during the analysis, based on their relative deviations from the reference intensity of background energy and the reference sensitivity;
   determining a measurement time, given a requisite lower detection limit, using the determined intensity of background energy and sensitivity, wherein the measurement time is a function of the requisite lower detection limit and the determined intensity of background energy and sensitivity; and
   proceeding with the analysis on the sample to conduct the analysis for a duration of the determined measurement time to thereby effect the requisite lower detection limit.

2. A method according to claim 1, wherein determining the reference intensity of background energy comprises:
   defining a function simulating a spectrum pattern exhibited by the reference sample; and
   calculating an area along the function.

3. A method according to claim 1, wherein the reference sample contains a reference element at a known concentration, and determining the reference sensitivity comprises determining the reference sensitivity, using the following equation:

$$Sensitivity = \frac{(GrossIntensity - BackgroundInstensity)}{Concentration}$$

where the gross intensity represents an intensity of peak energy at a spectral position of the reference element, the background intensity represents the reference intensity of background energy at the spectral position of the element and the concentration represents the known concentration of the element.

4. A method according to claim 2, wherein the function for determining measurement time is defined by the following equation:

$$lowerDetectionLimit = \frac{3 \times \sqrt{\frac{BGIntensity}{MeasurementTime}}}{Sensitivity}.$$

where "Lower Detection Limit" represents the requisite lower detection limit, "BG Intensity" represents the determined intensity of background energy for the analysis, "Measurement Time" represents the measurement time, and "Sensitivity" represents the determined sensitivity for the analysis.

5. A method according to claim 4, wherein the deviations are caused by at least one of a difference of the sample and a difference of operation parameters of the X-ray fluorescent analysis apparatus.

6. A method according to claim 5, wherein the sample contains at least one other element which is not contained in the reference sample, and the at least one other element causes at least the intensity of background energy for the analysis to deviate from the reference intensity of background energy.

7. A method according to claim 5, wherein the sample differs in size from the reference sample, and the difference in size causes both the intensity of background energy and sensitivity for the analysis to deviate from the reference intensity of background energy and sensitivity.

8. A method according to claim 5, wherein the X-ray fluorescent analysis apparatus irradiates an X-ray onto the sample at an intensity which differs from one at which an X-ray is irradiated onto the reference sample, and the difference in irradiation intensity causes at least at least the sensitivity for the analysis to deviate from the reference sensitivity.

\* \* \* \* \*

UNITED STATES PATENT AND TRADEMARK OFFICE
CERTIFICATE OF CORRECTION

PATENT NO. : 7,289,598 B2  
APPLICATION NO. : 11/264403  
DATED : October 30, 2007  
INVENTOR(S) : Yoshiki Matoba It is certified that error appears in the above-identified patent and that said Letters Patent is hereby corrected as shown below:

In the Claims

Column 6, in claim 8, line 50, after "irradiation intensity causes" delete "at least" (second occurrence).

Signed and Sealed this

Sixth Day of May, 2008

JON W. DUDAS  
*Director of the United States Patent and Trademark Office*